(12) United States Patent
Elliott

(10) Patent No.: US 7,571,658 B1
(45) Date of Patent: Aug. 11, 2009

(54) ASPHALT SAMPLING DEVICE

(76) Inventor: Norman Joseph Elliott, 8074 Rampart Cir., Mechanicsville, VA (US) 23111

( * ) Notice: Subject to any disclaimer, the term of this patent is extended or adjusted under 35 U.S.C. 154(b) by 463 days.

(21) Appl. No.: 11/593,920

(22) Filed: Nov. 7, 2006

(51) Int. Cl.
*G01N 1/04* (2006.01)
(52) U.S. Cl. .................................. 73/864.42
(58) Field of Classification Search . 73/864.41–864.44, 73/864.51, 864.52, 864.53, 864.73, 864.74
See application file for complete search history.

(56) References Cited

U.S. PATENT DOCUMENTS

| | | | | |
|---|---|---|---|---|
| 2,499,433 | A | * | 3/1950 | Waite et al. .................... 37/185 |
| 3,954,013 | A | * | 5/1976 | West ....................... 73/863.52 |
| 5,211,062 | A | * | 5/1993 | Moser ..................... 73/864.33 |
| 6,318,193 | B1 | * | 11/2001 | Brock et al. ............. 73/864.74 |

OTHER PUBLICATIONS

From the website of Pavement Technology Incorporated, Jan. 2006.

* cited by examiner

*Primary Examiner*—Robert R Raevis

(57) ABSTRACT

An articulated robotic hot asphalt sampling device comprising: a vertical base; a manually or automatically powered vertical shaft extending vertically from the base; a generally horizontal arm extending from the vertical shaft, having a first end proximate the vertical shaft and a second end remote from the vertical shaft and capable of pivoted vertical movement; a mechanism for pivotally vertically moving the generally horizontal arm; a sampling arm in the second end of the generally horizontal arm capable of upward and downward movement relative to the second end; a mechanism for moving the sampling arm upward and downward; a sampling bucket mounted to the sampling arm; a mechanism for opening and closing the sampling bucket; and a mechanism for controlling movement of the various elements of the sampling device.

7 Claims, 2 Drawing Sheets

ASPHALT SAMPLING DEVICE

The present invention relates to a device for sampling hot loads of asphalt and more particularly to such a device that allows for sampling without risk to the sampler.

BACKGROUND OF THE INVENTION

The sampling of truckloads of hot asphalt and aggregate for assay and quality control purposes is practiced at all asphalt production and processing plants. This process generally involves the removal of a representative sample of hot asphalt from each truckload as it leaves the production/processing facility. In the past such sampling involved an individual actually stepping onto or leaning over the hot asphalt load to obtain the sample by driving a suitable sampling device into the load and removing the sample therefrom. Such activity exposed the sampler to significant risk since the hot asphalt can be at temperatures exceeding 300° F. and is emitting fumes that could be noxious to the sampler.

While various apparatus have been designed and built to solve this problem, the devices of the prior art generally required that a vehicle containing hot asphalt be driven under a frame to which a sampling device was mounted thus restricting the area within which a sample could be taken and placing the apparatus operator in relative proximity to the hot asphalt. One example of such a device is marketed by Pavement Technology Incorporated of Grove Ill.

There thus remains a need for a device that is capable of sampling hot asphalt contained in an open haul vehicle wherever located. Such a device should allow for relative remote operation from a position where the operator is somewhat removed from the hot asphalt being sampled and ideally allows for positioning of haul vehicles in a variety of positions even on opposite sides of a centrally located sampling device.

OBJECT OF THE INVENTION

It is therefore an object of the present invention to provide a hot asphalt sampling device that allows for operator positioning relatively removed from the location of the haul vehicle and its attendant safety concerns.

It is another object of the present invention to provide a hot asphalt sampling device that provides a relatively broad operating footprint that allows for multiple or even relatively inaccurate positioning of a haul vehicle during the sampling operation.

SUMMARY OF THE INVENTION

According to the present invention, there is provided an articulated robotic hot asphalt sampling device comprising: a vertical base; a manually or automatically rotatably powered vertical shaft extending vertically from the base; a generally horizontal arm extending from the vertical shaft, having a first end proximate the vertical shaft and a second end remote from the vertical shaft and capable of pivoted vertical movement; a mechanism for pivotally vertically moving the generally horizontal arm; a sampling arm in the second end of the generally horizontal arm capable of upward and downward movement relative to the second end; a mechanism for moving the sampling arm upward and downward; a sampling bucket mounted to the sampling arm; a mechanism for opening and closing the sampling bucket; and a mechanism for controlling the various movements of the various elements of the sampling device. According to various preferred embodiments, the hot asphalt sampling device includes a hopper into which hot asphalt samples are placed after being withdrawn from a haul vehicle and a manual mechanism for rotating the vertical shaft.

DETAILED DESCRIPTION

Figure 1:
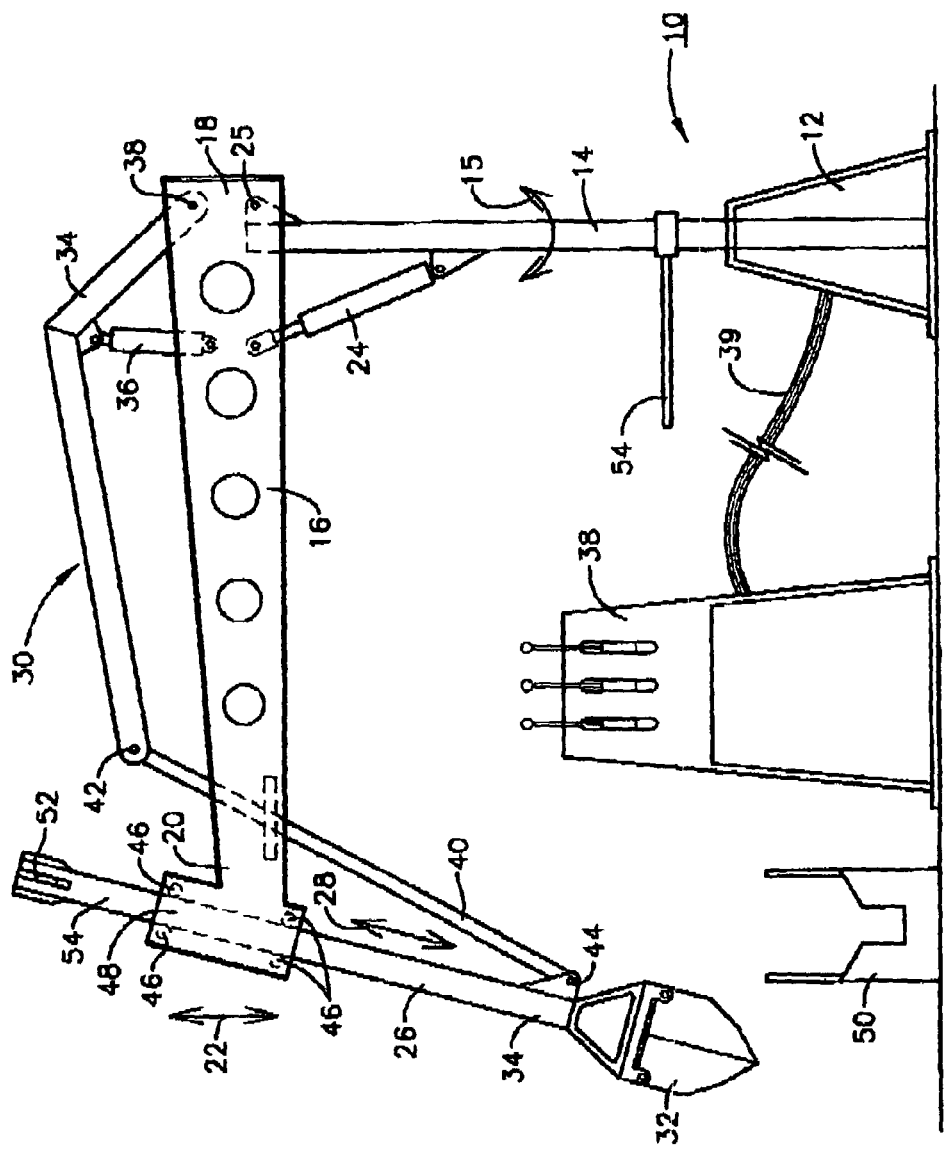
FIG. 1 is a side view of the hot asphalt sampling device of the present invention.

Referring now to the accompanying drawings, the hot asphalt sampling device 10 of the present invention comprises: a vertical base 12; a rotatable vertical shaft 14 extending from base 12 that rotates as indicated by arrow 15; a generally horizontal arm 16 having a first end 18 and a second end 20 capable of vertical movement in the directions shown by arrow 22 driven, according to the embodiment depicted in FIG. 1, by hydraulic cylinder 24 and pivoting about point 25 at first end 18; a sampling arm 26 capable of upward and downward movement relative to generally horizontal arm 16 in the direction of arrow 28 through the action of assembly 30 described more fully below; a clam shell sampling bucket 32 attached to the lower end 34 of sampling arm 26; and a control station 38 of conventional design and manufacture for operating the various elements of sampling device 10 via cables/hoses 39 as described more fully below.

Assembly 30 that imparts upward and downward movement to sampling arm 26 comprises a first angular drive arm 34 that is driven upward and downward by hydraulic cylinder 36 as it pivots about point 38 causing second drive arm 40 that is attached to lower end 34 and pivots about points 42 and 44 thereby causing sampling arm 26 to move upward and downward at end 20 of generally horizontal arm 16. According to the preferred embodiment of the invention depicted in FIG. 1, sampling arm 26 is of a rectangular shape and movement of sampling arm 26 is enabled through the action of rollers 46 within aperture 48 in second end 20 that engage the edges of rectangular sampling arm 26. According to the preferred embodiment of the sampling device 10 of the present invention shown in FIG. 1, the apparatus includes a hopper 50 for the receipt of hot asphalt samples obtained thorough the action of sampling bucket 32.

Figure 2:
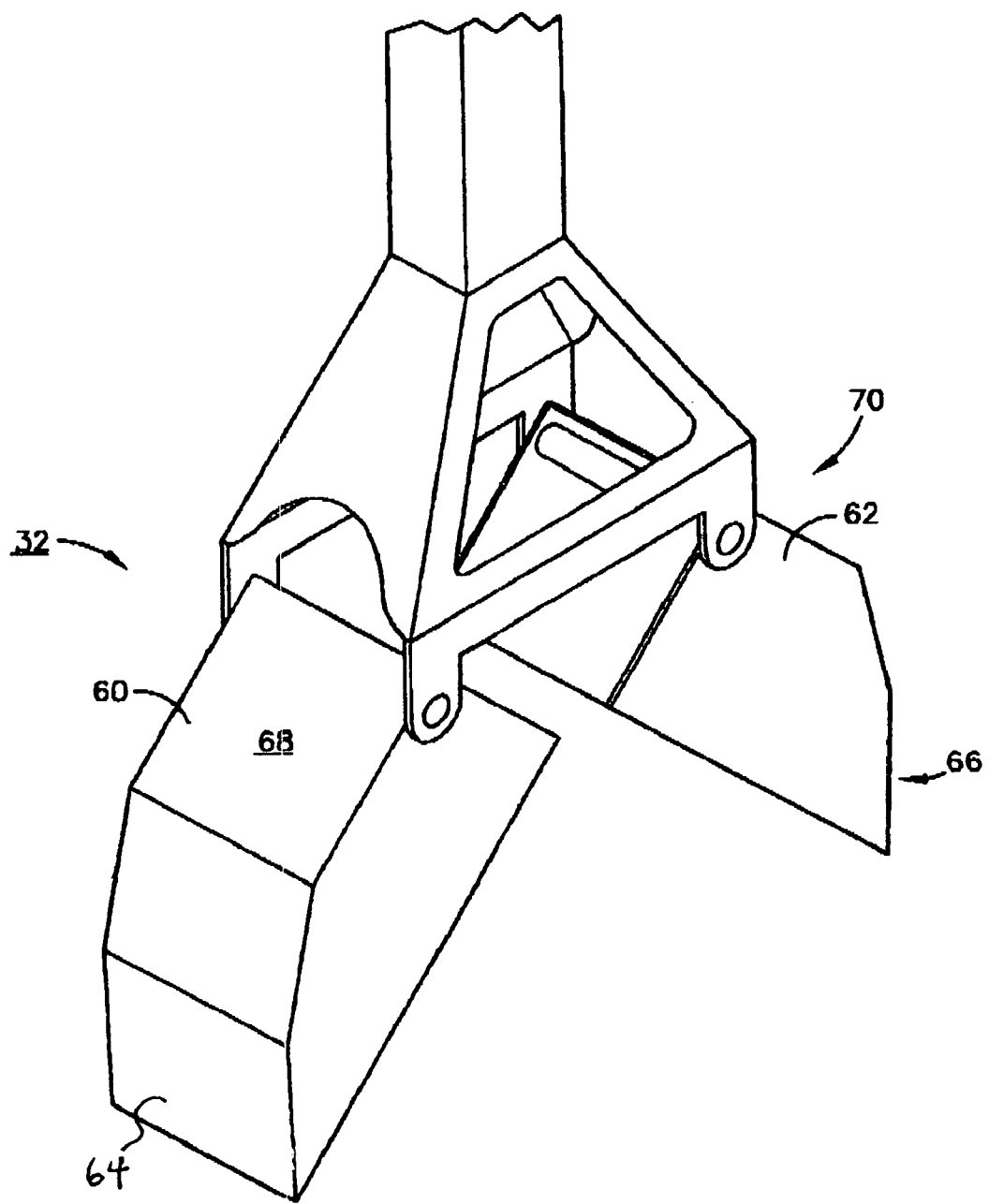
FIG. 2 is a perspective view of the sampling bucket of the hot asphalt sampling device of the present invention.

As shown in FIGS. 1 and 2, sampling bucket 32 is of the clam shell type. Opening (as shown in FIG. 2) and closing (as shown in FIG. 1) is achieved through the action of a drive system 52 that is preferably incorporated into sampling arm 26 at end 54, i.e. that end remote from sampling bucket 32, so that it is located as far away as possible from heat generated when sampling bucket 32 is filled with hot asphalt. Drive system 52 may comprise an electric motor, a hydraulic cylinder or the like, and any suitable drive system that can impart the opening and closing action to sampling bucket 32 should be considered as useful in accordance with the present invention.

According to the preferred embodiment depicted in FIG. 1, rotating shaft 14 is equipped with a manual steering arm 54 that allows an operator to rotate generally horizontal arm 16 to a location on either side of sampling device 10 prior to initiation of the sampling operation. It will be readily apparent to the skilled artisan that steering of generally horizontal arm 16 could also be accomplished with an automated system, however, the use of a manual steering system helps to assure that the operator remains close to base 12 and consequently away from any hot asphalt load being sampled.

With the structure just described it is apparent that virtually all of the heavier motors, pumps etc. required to operate sampling device 10 can be centrally located in or in the area of base 12 thereby reducing the load carrying capabilities of the various extended arms and reducing the cost and of construction of sampling device 10.

Referring now to FIG. 2 that depicts sampling bucket 32 of the present invention, sampling bucket 32 is of a clamshell design, comprising a pair of opposed halves 60 and 62 that pivot to open and close to form a closed bucket. Surfaces 64 and 66 of halves 60 and 62 are at approximately a 45 degree angle with respect to upright surfaces 68 and 70.

In use, sampling apparatus 10 acquires a hot asphalt sample by rotating sampling bucket 32 to a position over a haul vehicle located within the reach of generally horizontal arm 16, driving sampling bucket 32 into the load of the haul vehicle in the closed position depicted in FIG. 1 through the action of sampling arm 26, sampling bucket 32 opened within the load to the position depicted in FIG. 2, sampling bucket 32 again closed to obtain a contained sample, sampling arm 26 retracted, generally horizontal arm 16 rotated to a position over hopper 50, sampling arm 26 extended downward and the contained sample deposited into hopper 50 by the opening of sampling bucket 32. In this fashion, a clearly representative sample of the contained load can be readily and easily obtained without exposing the operator to the hot asphalt load.

As the invention has been described, it will be apparent to those skilled in the art that the same may be varied in many ways without departing from the spirit and scope of the invention. Any and all such modifications are intended to be included within the scope of the appended claims.

What is claimed is:

1. A hot asphalt sampling system comprising:
   A) a vertical base;
   B) a manually or automatically powered vertical shaft extending vertically from the base;
   C) a generally horizontal arm extending from the vertical shaft, having a first end proximate the vertical shaft and a second end remote from the vertical shaft and capable of pivoted vertical movement;
   D) a mechanism for pivotally vertically moving the generally horizontal arm;
   E) a sampling arm in the second end of the generally horizontal arm capable of upward and downward movement relative to the second end;
   F) a mechanism for moving the sampling arm upward and downward;
   G) a sampling bucket mounted to the sampling arm;
   H) a mechanism for opening and closing the sampling bucket; and
   I) a mechanism for controlling movement of each of elements A through H of the sampling system.

2. The hot asphalt sampling system of claim 1 wherein said sampling bucket comprises a clamshell that can be opened and closed to obtain a sample.

3. The hot asphalt sampling system of claim 2 wherein said mechanisms for pivotally vertically moving the generally horizontal arm and moving the sampling arm upward and downward comprise hydraulic cylinders.

4. The hot asphalt sampling system of claim 3 further including a hopper into which a sample obtained with the sampling bucket can be deposited.

5. The hot asphalt sampling system of claim 3 wherein said sampling arm includes a first end and a second end proximate said sampling buckets and said mechanism for moving the sampling arm upward and downward comprises a drive mechanism located at said first end.

6. The hot asphalt sampling system of claim 2 further including a hopper into which a sample obtained with the sampling bucket can be deposited.

7. The hot asphalt sampling system of claim 5 wherein said sampling arm is rectangular in cross section and includes edges, and said mechanism for moving the sampling arm upward and downward further comprises an aperture in the second end of the generally horizontal arm that also includes rollers that engage said edges and guide said sampling arm in its upward and downward movement.

\* \* \* \* \*